US012805794B2

(12) United States Patent
Mendes-Roter et al.

(10) Patent No.: US 12,805,794 B2
(45) Date of Patent: Nov. 24, 2026

(54) SYSTEM AND METHOD FOR PERFORMING AN AT-HOME PERIPHERAL ARTERIAL TONOMETRY

(71) Applicant: Itamar Medical, Ltd., Caesarea (IL)

(72) Inventors: Joao Mendes-Roter, Pardes Hana (IL); Eilon Livne, Binyamina (IL); Efrat Litman, Tel Aviv (IL); Shiri Shneorson, Ramat Hasharon (IL)

(73) Assignee: Itamar Medical Ltd., Caesarea (IL)

( * ) Notice: Subject to any disclaimer, the term of this patent is extended or adjusted under 35 U.S.C. 154(b) by 473 days.

(21) Appl. No.: 17/509,280

(22) Filed: Oct. 25, 2021

(65) Prior Publication Data

US 2022/0125377 A1 Apr. 28, 2022

Related U.S. Application Data

(60) Provisional application No. 63/105,604, filed on Oct. 26, 2020.

(51) Int. Cl.
*A61B 5/00* (2006.01)
*G16H 10/20* (2018.01)
*G16H 40/67* (2018.01)

(52) U.S. Cl.
CPC .......... *A61B 5/4818* (2013.01); *A61B 5/6823* (2013.01); *A61B 5/7475* (2013.01); *G16H 10/20* (2018.01); *G16H 40/67* (2018.01)

(58) Field of Classification Search
CPC ...... G16H 10/20; G16H 40/67; A61B 5/7475; A61B 5/6823; A61B 5/4818
See application file for complete search history.

(56) References Cited

U.S. PATENT DOCUMENTS

| | | | | |
|---|---|---|---|---|
| 10,426,399 | B1 | 10/2019 | Kayyali et al. | |
| 2011/0145747 | A1* | 6/2011 | Wong | A61B 5/7264 709/219 |
| 2016/0012194 | A1* | 1/2016 | Prakash | G06Q 30/0601 705/2 |
| 2016/0151603 | A1* | 6/2016 | Shouldice | A61B 5/486 600/26 |
| 2017/0135495 | A1 | 5/2017 | Hattori | |
| 2017/0209055 | A1* | 7/2017 | Pantelopoulos | A61B 5/02438 |

(Continued)

FOREIGN PATENT DOCUMENTS

| | | | | |
|---|---|---|---|---|
| EP | 2583248 | B1 | 10/2018 | |
| WO | WO-2016110804 | A1 * | 7/2016 | A61B 3/16 |

(Continued)

OTHER PUBLICATIONS

European Extended Search Report for EP Application No. 21885462.8, mailed on Aug. 30, 2024, 8 pages.

*Primary Examiner* — Amanda L Steinberg
(74) *Attorney, Agent, or Firm* — The Webb Law Firm

(57) ABSTRACT

A system and method for performing a remote sleep apnea test is provided. The method includes: determining, based on sensor measurements generated during a sleep apnea test, an end of the sleep apnea test, wherein the sensor measurements are generated by at least one sensor; rendering at least one post-test question via a user interface within a threshold period of time since the end of the sleep apnea test is determined; and capturing at least one input provided by the patient in response to the rendered at least one post-test question.

26 Claims, 8 Drawing Sheets

(56) References Cited

U.S. PATENT DOCUMENTS

| | | | | |
|---|---|---|---|---|
| 2018/0317839 | A1* | 11/2018 | Raymann .............. | H04L 67/535 |
| 2019/0000349 | A1 | 1/2019 | Narayan et al. | |
| 2019/0114321 | A1* | 4/2019 | Lam .................. | G06F 16/24522 |
| 2019/0290195 | A1 | 9/2019 | Lim | |
| 2020/0009349 | A1* | 1/2020 | Shouldice ............. | A61M 21/02 |
| 2021/0077013 | A1 | 3/2021 | Mistrorigo De Almeida | |
| 2021/0327584 | A1* | 10/2021 | Vakulin .................. | A61B 5/113 |
| 2023/0157631 | A1* | 5/2023 | Sletten ................. | A61B 5/4815 600/301 |
| 2023/0238150 | A1* | 7/2023 | Toth ....................... | G16H 50/80 705/2 |

FOREIGN PATENT DOCUMENTS

| | | | |
|---|---|---|---|
| WO | 2019134022 | A1 | 7/2019 |
| WO | 2020082115 | A1 | 4/2020 |

* cited by examiner

700

Main Complaints

702

- 704 ☐ Trouble falling asleep
- 704 ☐ Trouble remaining asleep
- 704 ☐ Excessive sleepiness during the day
- 704 ☐ Snoring
- 704 ☐ Stop breathing during sleep
- 704 ☐ Unwanted behaviors during sleep, such as Acting out on your dreams, sleep walking, etc.
- 704 ☐ Spouse/Bed Partner wants me to be tested

PRIOR SLEEP DISORDER DIAGNOSIS OR STUDIES

702

Do you have a prior sleep diagnosis?

704 ☐ Insomnia ☐ Sleep Apnea Mild/Moderate/Severe ☐ Circadian

SLEEP PATTERN

702

- Typical bedtime: ________________ 706
- Typical amount of time it takes to fall asleep ______ 706 hours
- Typical hours in bed: ____________ hours. 706
- Typical hours of sleep: __________ 706 hours

BREATHING

702

- Have you been told that you snore? Yes/No o IF YES: Do you Snore Loudly (loud enough to be heard through closed doors or your bedpartner elbows you for snoring at night)? Yes/No

- Has anyone Observed you Stop Breathing or Choking/Gasping during your sleep ? Yes/No
- Do you have morning headaches? Yes/No
- Do you wake up in the morning with a dry mouth? Yes/No
- Do you have or are you being treated for high blood pressure? Yes/No
- Have you been diagnosed with heart failure? Yes/No

DAYTIME SLEEPINESS

702

1. Do you often feel Tired, Fatigued, or Sleepy during the daytime (such as falling asleep during driving or talking to someone)?
2. Do you feel unrefreshed or tired in the morning despite sleeping at night?
3. Do you have uncontrollable urges to fall asleep during the day?
4. Have you fallen asleep while driving?

If YES in any of questions (1-4) -> OPEN Sleepiness Scale Test Questions 708

FIG. 7

SYSTEM AND METHOD FOR PERFORMING AN AT-HOME PERIPHERAL ARTERIAL TONOMETRY

CROSS-REFERENCE TO RELATED APPLICATIONS

This application claims the benefit of U.S. Provisional Application No. 63/105,604 filed on Oct. 26, 2020, the contents of which are hereby incorporated by reference.

TECHNICAL FIELD

The disclosure generally relates to sleep apnea testing, and particularly to devices and methods for performing sleep apnea detection testing at a patient's home.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section. Similarly, issues identified with respect to one or more approaches should not assume to have been recognized in any prior art on the basis of this section, unless otherwise indicated.

Sleep disorders, such as sleep apnea, require testing and monitoring done in a laboratory with a skilled technician monitoring one or more patients while the patients sleep through the night. The technician may be responsible, among others, for ensuring placement of sensor devices on the monitored patient, monitoring the signals received from the sensor devices, and recording additional information, for example by asking patients to respond to surveys or questions before and after the testing. Lately, at-home testing devices have become available, allowing a patient to conduct a test at home. However, conducting tests at home are not without drawbacks, such as lack of real time professional monitoring and a reduced clinical environment.

As sleep disorders may be linked to vascular health issues, it would be beneficial to provide access to testing to as large a population as is medically viable. However, there is a limitation of both skilled technicians and physical space in a laboratory which hinder such access. It would therefore be beneficial to provide a solution to the challenges noted above.

SUMMARY

A summary of several example embodiments of the disclosure follows. This summary is provided for the convenience of the reader to provide a basic understanding of such embodiments and does not wholly define the breadth of the disclosure. This summary is not an extensive overview of all contemplated embodiments, and is intended to neither identify key or critical elements of all embodiments nor to delineate the scope of any or all aspects. Its sole purpose is to present some concepts of one or more embodiments in a simplified form as a prelude to the more detailed description that is presented later. For convenience, the term "certain embodiments" may be used herein to refer to a single embodiment or multiple embodiments of the disclosure.

Certain embodiments disclosed herein include: a method for performing a remote sleep apnea test. The method comprises determining, based on sensor measurements generated during a sleep apnea test, an end of the sleep apnea test, wherein the sensor measurements are generated by at least one sensor; rendering at least one post-test question via a user interface within a threshold period of time since the end of the sleep apnea test is determined; and capturing at least one input provided by the patient in response to the rendered at least one post-test question.

Certain embodiments disclosed herein include a system for performing a remote sleep apnea test. The system comprises a processing circuitry; and a memory, the memory containing instructions that, when executed by the processing circuitry, configure the system to: determine, based on sensor measurements generated during a sleep apnea test, an end of the sleep apnea test, wherein the sensor measurements are generated by at least one sensor; render at least one post-test question via a user interface within a threshold period of time since the end of the sleep apnea test is determined; and capture at least one input provided by the patient in response to the rendered at least one post-test question.

BRIEF DESCRIPTION OF THE DRAWINGS

The subject matter of the disclosure is particularly pointed out and distinctly claimed in the claims at the conclusion of the specification. The foregoing and other objects, features and advantages will become apparent and more readily appreciated from the following detailed description taken in conjunction with the accompanying drawings.

FIG. 7 is a non-limiting example of a questionnaire according to an embodiment.

DETAILED DESCRIPTION

Figure 1A:
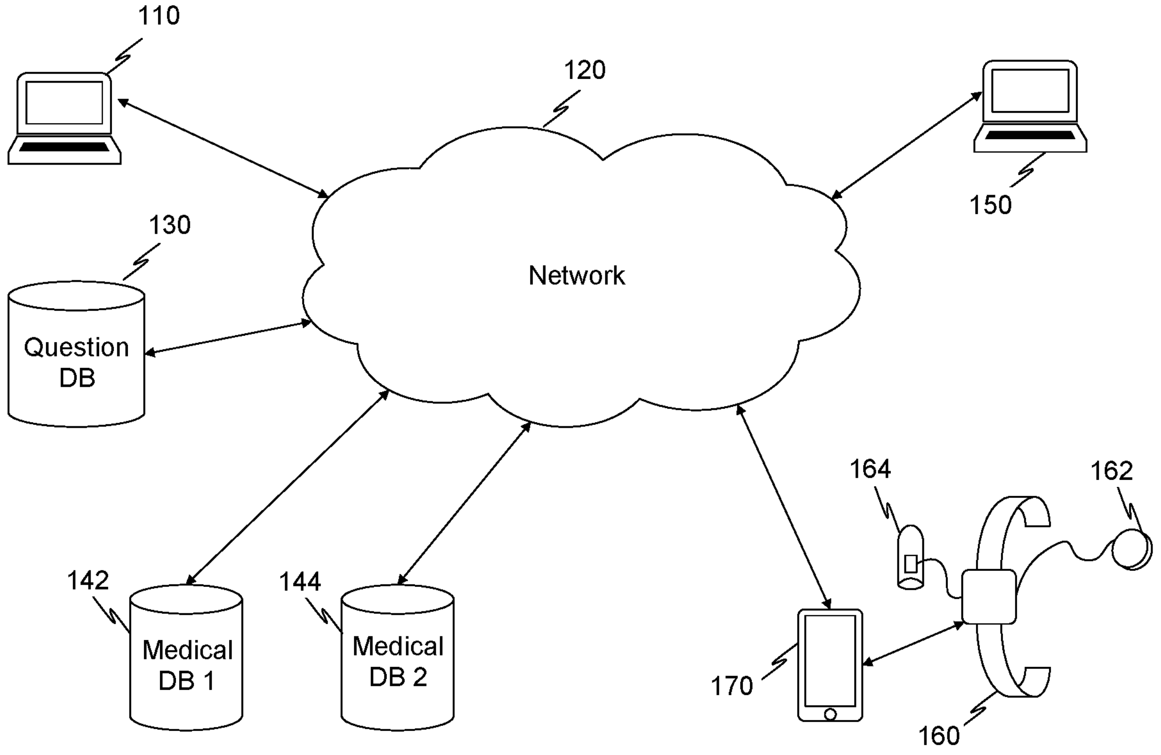
FIG. 1A is a network diagram utilized to describe various disclosed embodiments.

Below, embodiments will be described in detail with reference to accompanying drawings so as to be easily realized by a person having ordinary knowledge in the art. The embodiments may be embodied in various forms without being limited to the examples set forth herein. Descriptions of well-known parts are omitted for clarity, and like reference numerals refer to like elements throughout.

It is important to note that the embodiments disclosed herein are only examples of the many advantageous uses of the innovative teachings herein. In general, statements made in the specification of the present application do not necessarily limit any of the various claims. Moreover, some statements may apply to some inventive features but not to others. In general, unless otherwise indicated, singular elements may be in plural and vice versa with no loss of generality.

A development of an at-home sleep apnea test enables monitoring of a large population of patients for their sleep pattern and possibly related cardiovascular health issues. Unlike conventional sleep tests at a medical facility, the disclosed techniques for sleep tests can be performed from the comfort of the patient's home, under conditions that closely resemble their normal sleep condition. It has been identified, however, that the absence of trained technicians for simultaneous observation of testing, may result in an incomplete sleep test. Accordingly, the disclosed embodiments provide a method and system for remote apnea sleep test that performs peripheral arterial tonometry and utilizes such data for immediate feedback to the patient and the remotely monitoring physician for a more comprehensive test result.

Additionally, it has been identified that asking a patient questions at a time that is remote from when the sleep test was performed results in less accurate answers and, accordingly, decreases the ability to diagnose and treat sleep-related medical conditions. Accordingly, the disclosed embodiments further include techniques for timing questions to be asked in relation to a sleep test based on sensor readings during the sleep test which allows for maximizing the accuracy of the patient's recollection and, consequently, their responses.

The disclosed embodiments include techniques for detecting sleep using a sensor assembly and recording inputs with respect to questions answered by the patient. Information as such is actively communicated to the patient, physician, database, and the like, to improve timing and quality of questions that are rendered to the patient. In an embodiment, the timing and content of questions are adjusted depending on prior data input from patient's answers, sleep detection, or both. Furthermore, unnecessary or redundant questions may be removed, and patient-specific questions, condition-specific questions, or both, may be presented. In another embodiment, physicians may directly participate in the test by responding to collected data and communicating with the questionnaire database, the sensor assembly, and the like. In yet another embodiment, the questions may be rendered immediately before a sleep period, after the sleep period, or both, removing uncertainty from possible human errors that may occur with time lapse. The disclosed embodiments provide a system for at-home sleep test in order to improve sleep test accuracy and in return discovery and treatment of associated vascular health issues. In particular, various disclosed embodiments improve quality and timing of questions rendered to patients by incorporating the sensor assembly, utilizing its data and allowing simultaneous/instantaneous communication during remote monitoring and recording of sleep.

In an embodiment, a system for at-home sleep apnea testing includes a sensor assembly which is assigned to a unique user. The unique user is presented with one or more questionnaires in connection with a series of measurements by the sensor assembly. A questionnaire may include multiple questions to which the user may provide inputs through a user interface. Questions may be added or subtracted from the questionnaire by rendering requests for inputs for the user interface based on inputs received from the user. A questionnaire may be generated for a user based on patient information and instructions received from a physician user device. The physician user device may communicate with a questionnaire database. In an embodiment, the questionnaire database may include metadata, such as metadata indicating clustering of questions based on patient attributes. Questions may be generated for the physician device based, for example, on the question clusters and patient information.

Figure 1B:
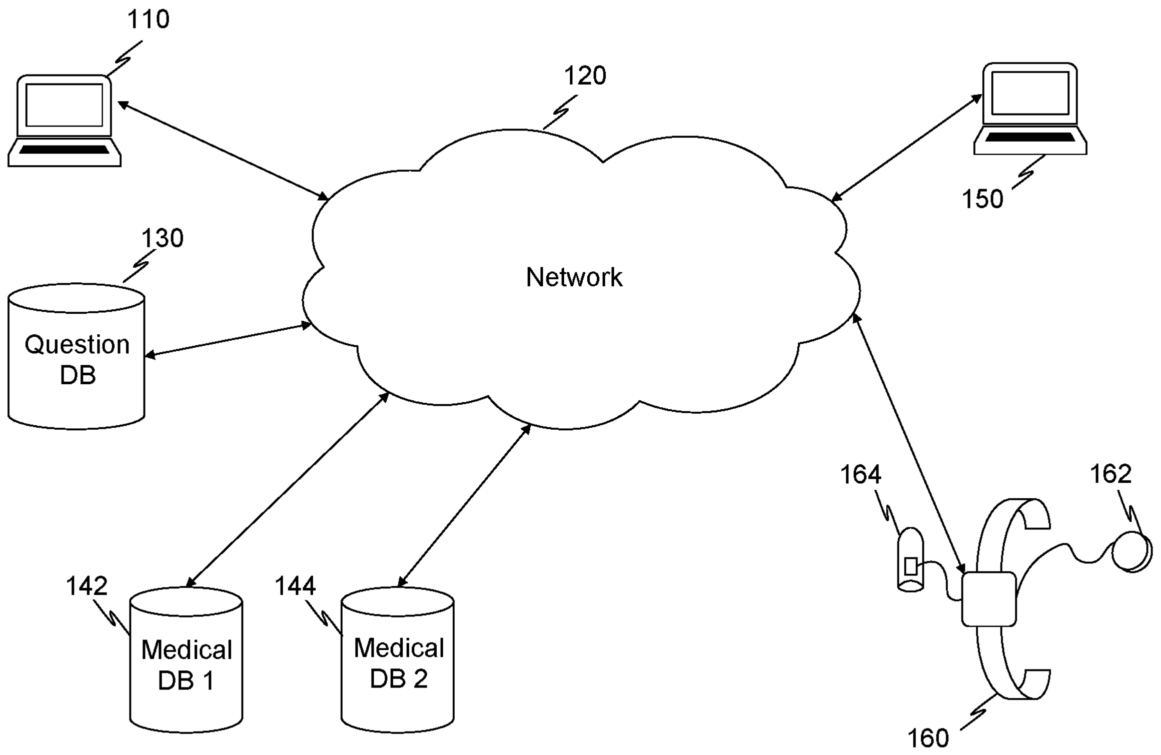
FIG. 1B is another network diagram utilized to describe various disclosed embodiments.

FIG. 1A is a network diagram utilized to describe various disclosed embodiments. Reference is also made to FIG. 1B which is another network diagram utilized to describe various disclosed embodiments. A physician computing device (PCD) 110 is communicatively connected to a network 120. In an embodiment, the network 120 may be configured to provide connectivity of various sorts, as may be necessary, including but not limited to, wired and/or wireless connectivity, including, for example, local area network (LAN), wide area network (WAN), metro area network (MAN), worldwide web (WWW), Internet, and any combination thereof, as well as cellular connectivity. The PCD 110 may be a laptop computer, a desktop computer, a tablet, and the like computing device which may have a display, an input interface, and a network interface for communicating with and through the network 120.

The PCD 110 may include, or may be configured to communicate, with a questionnaire database (question DB) 130. The questionnaire database 130 may store data indicating a plurality of questions which may be organized in question groups. A question group includes one or more questions. An operator of the PCD 110 may select, through a user interface (for example, the user interface discussed in more detail below with respect to FIG. 2) one or more question groups or individual questions, directed to a patient.

The operator of the PCD 110 may select different questions, or different question groups, for each patient. A group of questions which are selected for (and therefore are associated with) a patient are referred to as a questionnaire. In an embodiment, questionnaires may be associated with either a pretest or post-test sequence (or both). An operator of the PCD 110 may further elect to add questions or question groups to the questionnaire database 130. The PCD operator may also associate a plurality of questions, thereby generating a question group. In this manner, a group of questions (for example recurring questions such as 'what is your name', 'what is your age', etc.) may be more easily added to future questionnaires. A question is a prompt for input from a user. A question may include a text portion to explain to a user what input is required, and an input field. The input field may be, for example, a checkbox, a textual input, a dropdown list, and the like. In an embodiment, the PCD 110 may send a questionnaire to a user device, such as user device 170, which is operated by a patient. In some embodiments, the PCD 110 may configure the questionnaire to be sent to a primary sensor device 160 (e.g., as described in FIG. 1B).

The primary sensor device 160 is coupled with a position sensor 162 and a finger probe 164 (all together referred to as the sensor assembly). In an embodiment, the sensor assembly includes a network interface controller, a display to present questionnaire and requestions, and an input interface to receive input from a user. The finger probe 164 generates measurements based on detection of peripheral arterial tone. In certain embodiments, a photoplethysmogram (PPG) signal generator may be utilized in place of, or in addition to, the finger probe 164. In another embodiment, the primary sensor device may be coupled to a chest sensor, an accelerator, and other like sensors that measure human position or movement.

While FIGS. 1A-B are discussed with respect to a specific type of home sleep apnea test (HSAT) device, it should be understood that any such HSAT may be used, with appropriate sensors, without departing from the scope of this disclosure. A non-limiting example of such a HSAT device is described in more detail in U.S. Pat. No. 10,842,395 to Schnall et al., assigned to the common assignee, the contents of which are hereby incorporated by reference.

In various embodiments, the primary sensor device 160 includes a control circuit, a power source, and a communication interface (not shown). The communication interface may provide connectivity between the primary sensor device 160, the position sensor 162, and in some embodiments a user device. 170. In certain embodiments (for example, as shown in FIG. 1B) the primary sensor device 160 may provide connectivity to the network 120. The primary sensor device 160, the position sensor 162, the finger probe 164, and, where applicable, the user device 170 may be collectively referred to as the client system. The client system is configured to communicate over the network 120, and may establish communication, for example, with the PCD 110, or an administrative device 150.

In an embodiment, the administrative device 150 is configured to maintain a table (or other electronic or digital record) of unique identifiers of sensor assemblies, primary sensor devices 160, position sensors 162, finger probes 164, or any combinations thereof. A PCD 110 may assign a sensor assembly to a unique user account associated with a patient, who is the user of the sensory assembly, and in some embodiments the user of the user device 170. The table may indicate the unique identifier of each sensor assembly and its assigned unique user.

The network 120 further provides connectivity to one or more medical databases (medical DBs), such as a first medical DB 142 and a second medical DB 144. The first medical DB 142 may be physically located in a first location subject to a first jurisdiction, while the second medical DB 144 may be physically located in a second location subject to a second jurisdiction, and data is stored in any particular medical DB only as needed (e.g., to store data of a patient who is located in that jurisdiction). For example, the United States and European Union have different requirements for retaining and maintaining databases of patient information. By having a physical database at a location of each jurisdiction, certain legal requirements may be fulfilled. Thus, when a sensor assembly transmits information generated by the sensor assembly, the information may be stored at the relevant medical DB. A relevant medical DB may be assigned, for example, by the PCD 110 when associating a sensor assembly with a unique patient.

Figure 2:
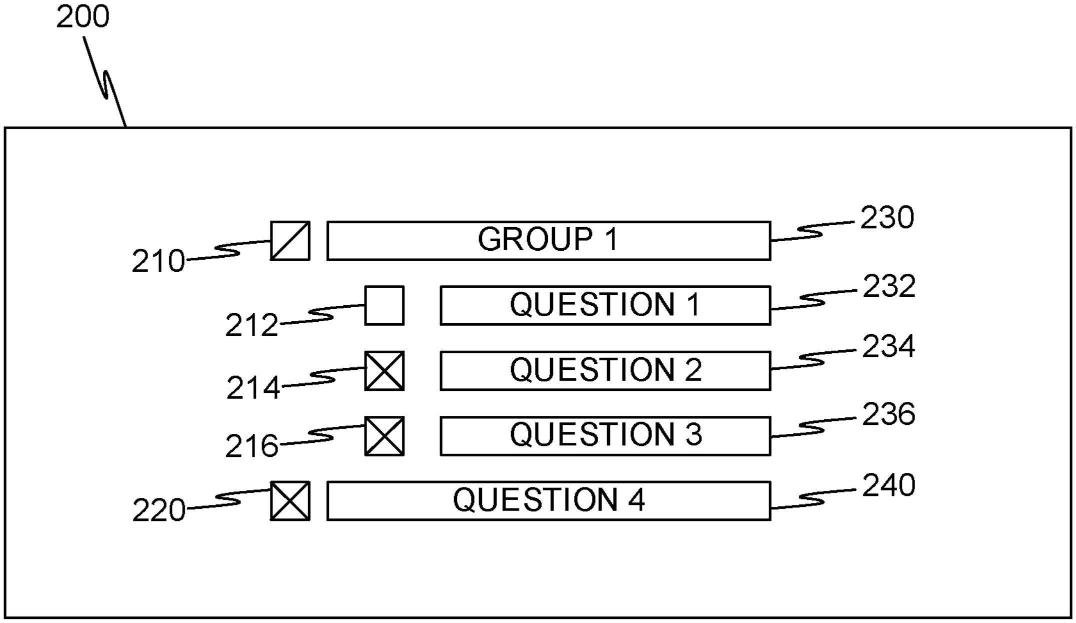
FIG. 2 is an illustration of a graphical user interface for configuring a patient questionnaire according to an embodiment.

FIG. 2 is an illustration of a graphical user interface 200 for configuring a patient questionnaire according to an embodiment. The GUI 200 includes a plurality of questions as may be displayed on the PCD 110, FIG. 1. In this example, the GUI includes a first question group 230, which is associated with a first question 232, a second question 234, and a third question 236. The GUI further includes a fourth question 240 which is not associated with the first group 230. In this example, association of a question with a group is done by rendering the question field with an indentation with respect to the group field, however it should be readily understood that other visual cues may be used.

Question groups may be linked, in a database (e.g., the question database 130, FIG. 1), to one or more groups (i.e., each question may be part of one or more groups). Each element in the database (e.g., group or question) may include an indicator, such as a checkbox, which can receive an input and be toggled between a first position (indicating that the question should be added to a questionnaire) and a second position (indicating that a question is not part of the questionnaire). For example, question 234 is associated with checkbox 214, and questions 232 is associated with checkbox 212. The former is marked, indicating that question 234 is part of the questionnaire, while the latter is unmarked, indicating that question 232 is not part of the questionnaire. Once questions have been selected for the questionnaire, the questionnaire may be sent to a user device or a sensor assembly associated with a particular user. The user in this example is a patient who is being monitored. In an embodiment, a question, or group of questions, may be included in the questionnaire, and configured to be displayed only in response to receiving a certain input to another question.

The questionnaire may be dynamic, adaptive, or both. A questionnaire is dynamic where the questions will vary based on an input from the PCD. A questionnaire may be adaptive where questions will further change (e.g., added or subtracted from the questionnaire) based on input received to other questions in the questionnaire, based on inputs generated by the sensor assembly, or a combination thereof. Such properties of the questionnaire are enabled by simultaneous and active communication between the various embodiments to improve quality of questions (or timing of asking questions), and further improve identification of sleep apnea in patients.

In an embodiment, when a sensor assembly initializes a test, the sensor assembly may attempt to communicate over a network with an administrator device (e.g., the admin device 150) or a physician computing device (e.g., the PCD 110) to ascertain what questionnaire, or group of questionnaires, to render for a user. In an embodiment, the sensor assembly (or user device) may communicate with an administrator device (or server) which may issue a challenge to the sensor assembly or a user device communicatively connected with the sensor assembly, to ascertain that the unique sensor assembly matches the user account. When such a challenge is issued, questions are only rendered to the patient if the challenge is successfully completed. A challenge may be successfully completed when, for example, an input indicating a required response (e.g., a required password or identifier) is received from the patient. For example, the administrator device may require a personal identification number (PIN) or password to begin the test, which is given by the physician to the patient. This ensures that the test is performed by the intended subject, and that the device is configured to send data to an authorized medical database. When a password or PIN is received, for example from the sensory assembly, the password or PIN can be matched to another identifier associated with the sensor assembly (e.g., a known password or PIN associated with the sensor assembly), and a questionnaire is only provided to the sensor assembly when the passwords or PINs match.

Figure 3:
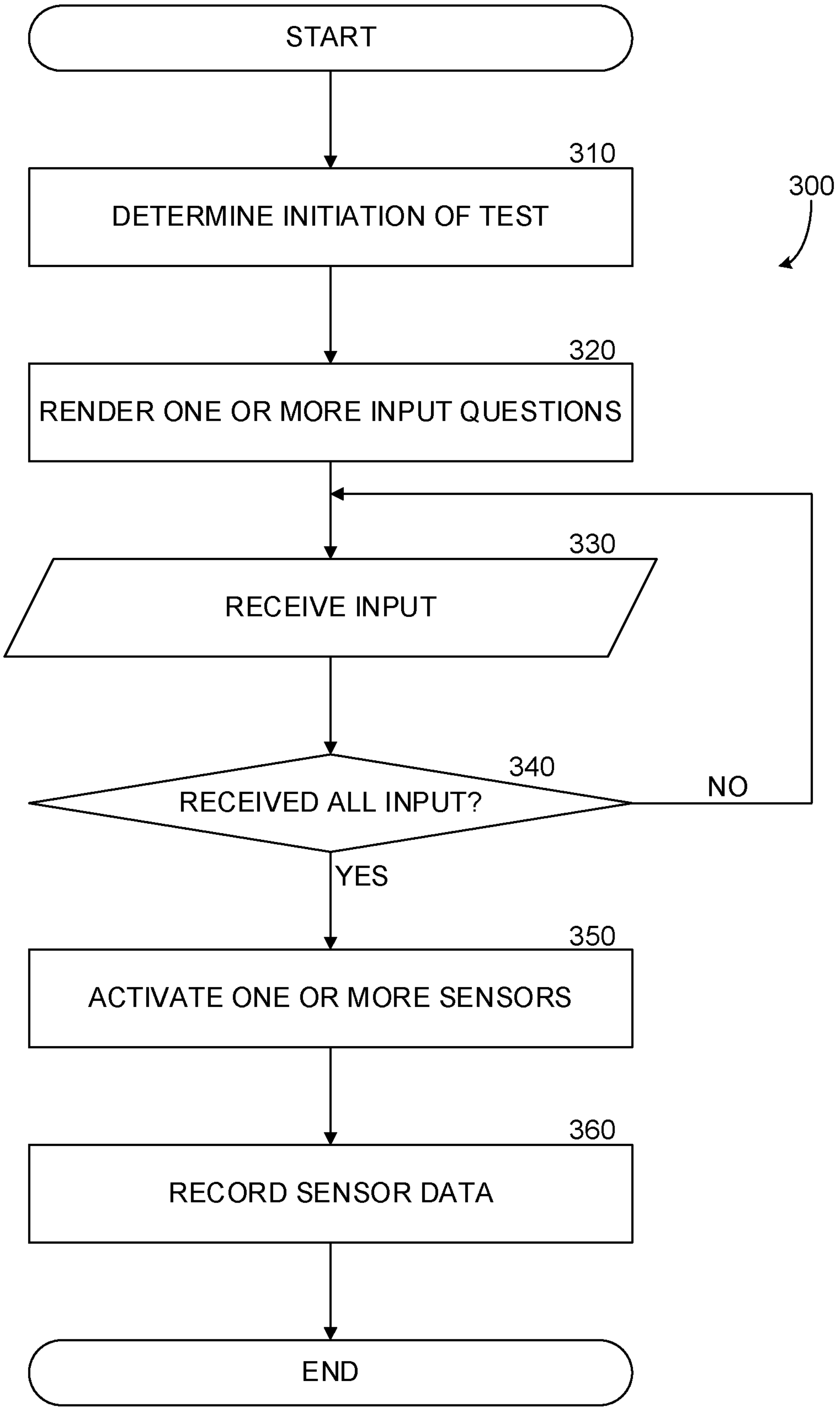
FIG. 3 is a flowchart of a method for initializing an at-home sleep apnea test according to an embodiment.

FIG. 3 is a flowchart 300 of a method for initializing an at-home sleep apnea test according to an embodiment. In an embodiment, the method is performed by the primary sensor device 160 or the user device 170, FIG. 1.

At S310, it is determined that a test is initialized. The test may be initialized by a user, for example by powering up a sensor assembly, by sending a request to an administrator device (or server) to initiate a test, and the like. The test includes a questionnaire and a sleep period during which the sensor assembly generates information based on sensor data and sends the sensor data to a medical database, where it may be accessed by a diagnostician or physician. In an embodiment, a questionnaire may be presented before, after, or both before and after, the sleep period.

At S320, a questionnaire including one or more input questions is rendered on a display that is communicatively connected to the sensor assembly. In some embodiments, the display may be a component of the sensor assembly. In certain embodiments, the display may be a component of a user device which is communicatively connected to the sensor assembly. The user device may render a user interface where questions are presented and a user of the user device may provide input according to the inputs of the user device, which may be, for example, a touchscreen, a button, a keyboard, one or more audio frames, video frames, and the like. The questionnaire may be downloaded from an administrator device or a physician computing device (PCD). In an embodiment, a physician computing device may instruct the sensor assembly to download certain questions from a question database. Such an instruction set would result in creation of a questionnaire using the questions downloaded from the question database.

At S330, one or more inputs are received for the one or more rendered input questions. In some embodiments, questions may be presented sequentially (i.e., a second question is rendered on the display only after input for the first question is received). In certain embodiments, a question may be rendered based on an input received for a previous question. For example, the question may be 'Do you smoke?'. If the input is 'no', then a next question may be rendered. If the input is 'yes', a follow-up question may be rendered, such as 'How many cigarettes do you smoke per day?'. In an embodiment, a plurality of follow-up questions (or sub-questionnaire) may be rendered in response to an input received for a given question. For example, a patient (e.g., a user of the user device) may indicate by input that they feel tired or drowsy during the day. Based on this input, a sleepiness assessment questionnaire, such as Sleepiness Assessment Test, may be provided to the user device.

At S340, a check is performed to determine if all input has been received. If 'no,' execution may continue at S330, to continue and receive input for all questions for which input has not been received. In an embodiment, a user device or the sensor assembly may generate a notification (which may be visual, audible, or a combination thereof) if it is determined that not all input has been received. If 'yes,' execution continues at S350. In an embodiment, a question may be rendered as part of an initial questionnaire, and be in a state where no input was received prior to beginning the test (i.e., generation of measurements). In such an example, the question may not be mandatory for the initial phase of the test, but mandatory at the end of the test.

At S350, one or more sensors of the sensor assembly are activated, to begin generating measurements based on sensor input. In some embodiments, a first group of sensors may be initially activated, and a second group of sensors may be activated in response to sensor signals captured by one or more sensors of the first group of sensors. For example, a heart rate monitor may sense a drop in heart rate, indicating that a patient is at or near sleep, which is a trigger to activate a second group of sensors which begin to record data. Thus, the energy storage of the sensor assembly is conserved, allowing for a longer test period.

In this regard, it is noted that at home sleep monitoring may require use of home sensor devices which may run on battery or other limited power sources whose power may expire prior to conclusion of the sleep period if all sensors are utilized for the entire duration of the sleep period. Accordingly, selectively activating sensors only as needed allows for increasing the likelihood that any tests using such limited power sensor devices are fully completed.

At S360, sensor data is recorded. Recording sensor data may include sending the data to a medical database according to a received conveyance from an administrator device. The recorded data may be reviewed by a diagnostician having access to the medical database.

Figure 4:
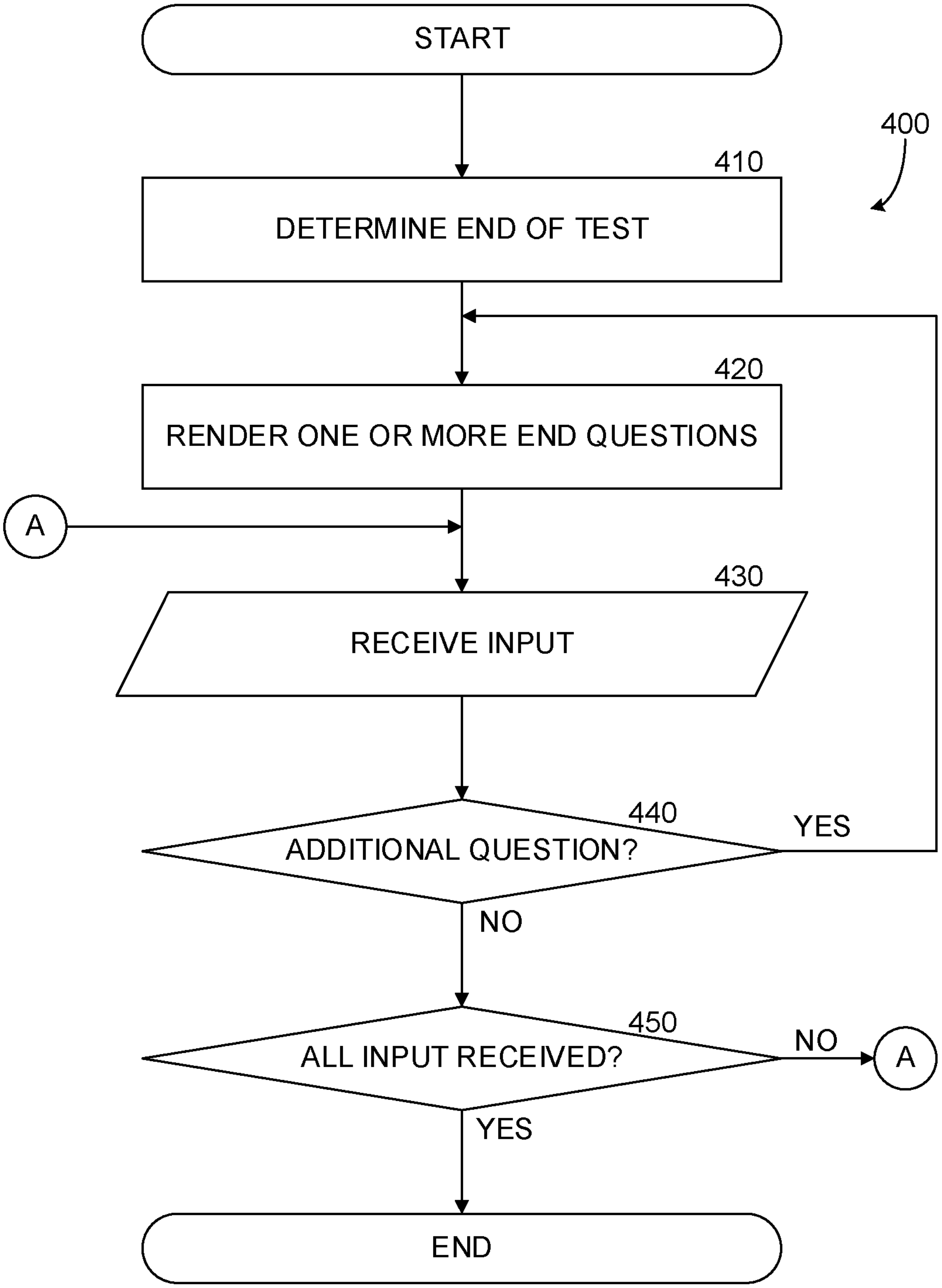
FIG. 4 is a flowchart of a method for concluding an at-home sleep apnea test according to an embodiment.

FIG. 4 is a flowchart 400 of a method for concluding an at-home sleep apnea test according to an embodiment. In an embodiment, the method is performed by the primary sensor device 160 or the user device 170, FIG. 1.

At S410, it is determined that a sleep portion of the test has concluded. Such a conclusion may be determined using a sensor assembly, for example, based on movement sensed by the sensors (which corresponds to being awake), by determining a time of day, a combination thereof, and the like. In some embodiments, it may be determined that the sleep portion has concluded based on detecting removal of one or more sensors from the patient's body (e.g., by ceasing to detect a signal generated from the sensor, or detecting 'noisy' signals). In certain embodiments, sensor removal may be a prerequisite, as it is possible that during the sleep portion of the test a patient awakens, for example to go to the bathroom during the night. In an embodiment, a patient may manually input a termination command to indicate that the sleep portion of the test has terminated.

At S420, one or more end questionnaires including one or more end questions are rendered on a display communicatively connected to the sensor assembly. As in FIG. 3 above, a test may include an initial questionnaire, an end questionnaire, or any combination thereof.

In an embodiment, the end questionnaires are rendered soon after the end of the test is determined (e.g., within a threshold period of time of such determination). In a further embodiment, the end questionnaires are rendered immediately after the end of the test is determined (i.e., as soon as possible once the end of the test has been determined). By rendering the end questionnaire within a threshold period after completion of the test, accuracy of the patient's answers can be maintained, thereby allowing for effectively performing an at home sleep apnea test. As noted above, such at home tests may result in inaccurate information gathering when the patient is asked questions long after the actual test, e.g., at a doctor's appointment the following day or later in the week. Thus, rendering and recording questions earlier improves the accuracy of the data and, therefore, allows for more accurate diagnosis and treatment. In other embodiments, the end questionnaires become unavailable after a second predetermined period of time has lapsed. This may be beneficial, for example, to avoid receiving answers which may be inaccurate due to a long time having passed since the events. In yet another embodiment, a timestamp may be associated with each received answer, which can be used by a physician to determine if the received answer is deemed by the physician accurate enough, given the time that lapsed between the event and between the patient's received answer.

At S430, input is received from an input interface communicatively connected to the sensor assembly. In an embodiment, the input interface may be a touchscreen of a smartphone which is communicatively connected to the sensor assembly.

At S440, a check is performed to determine if there are additional questions. Questions may be presented sequentially (i.e., a second question is rendered on the display only after input for the first question is received). In certain embodiments, a question may be rendered based on an input received of a previous question. In some embodiments, questions may be based on sensor inputs or detected events. For example, if a movement sensor indicates that a patient was awake 3 times during the night (for example by detecting a motion pattern from an accelerometer and comparing the detected motion pattern to existing motion patterns which are indicative of a state of being awake or asleep), the input interface may render a question 'Did you wake up 3 times during sleep?' or 'How many times do you remember waking up and getting out of bed during the night?'. If there are additional questions, execution continues at S420, otherwise execution continues at S450.

At S450, a check is performed to determine if input has been received for all required questions. In some embodiments, an input for a particular question is immediately transmitted to a medical database (e.g., one of the medical databases 142 or 144, FIG. 1). This may be beneficial, for example, due to patients neglecting to finish their questionnaire. If questionnaires are sent only once all questions are completed, then partial questionnaires would not be sent. However, it may be beneficial to have a partially completed questionnaire, if the alternative is no questionnaire input at all. If all input is not received, execution continues at S430. If all input is received, the input may be transmitted to the medical database, after which execution terminates. In some embodiments, a physician using a PCD may receive information from the sensor assembly and input from the patient. The physician may send through the PCD an additional questionnaire, for example based on initially reviewing and analyzing the information and determining that additional information is required. The questionnaire may be sent from the PCD to a user device of the patient to be rendered thereon. This may be performed numerous times, as needed by the physician.

In certain embodiments, a notification may be generated for the PCD, for the client device, or for both. A notification may be generated based on one or more signals detected by the sensor assembly. For example, the generated notification may include comorbidity information if sleep apnea is detected. Examples of comorbidities may include increased cardiovascular risks, obesity, and diabetes. The notification may be generated further based on the one or more signals, patient information, and questionnaire response(s).

In an embodiment, output from the sensor assembly may be cross referenced with data from one or more sleep study results. A sleep study result may be a model which, for example, clusters patients based on attributes (e.g., diagnoses, age, gender, weight, etc.) and symptoms and assigns a probability for certain symptoms to be correlated with one or more attributes. A notification may be generated to indicate that based on the sensor assembly output and a sleep study model, a certain symptom has a probability to occur. The notification may be generated for the PCD, the client device, or both.

Figure 5:
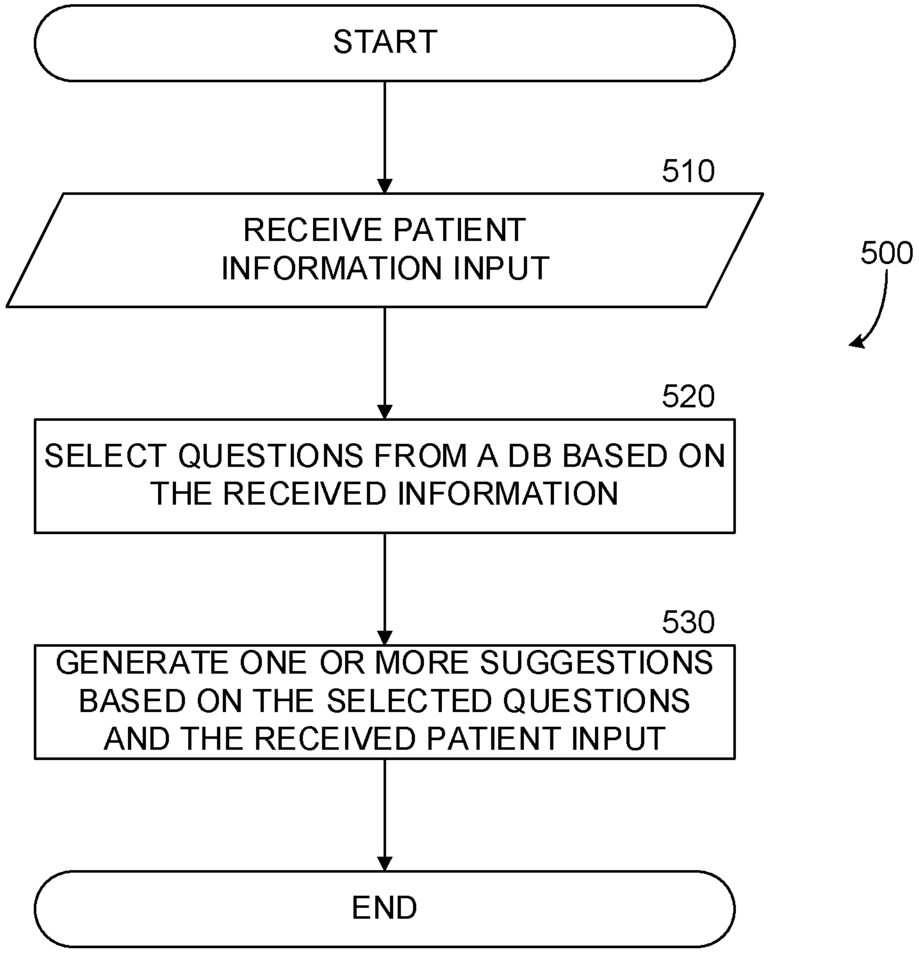
FIG. 5 is a flowchart of a method for automatically generating a questionnaire according to an embodiment.

FIG. 5 is a flowchart 500 of a method for automatically generating a questionnaire according to an embodiment.

At S510, patient information input is received. Patient information may include, for example, data (such as sex, age, weight, etc.), results of previous questionnaires, results of previous HSATs, analysis of results, and the like. Patient information may be structured, or may be unstructured such as natural language entered by a physician or caretaker.

At S520, one or more questions are selected from a questionnaire database based on the patient information input. In an embodiment, selection may include clustering the patient in one of a plurality of patient clusters. Each patient cluster includes one or more similar characteristics of a patient, for example based on patient data (e.g., all patients age 50 and over). A system may determine one or more questions which were present in questionnaires presented to patients of the patient cluster. In certain embodiments, a system may perform natural language processing, or determine keywords entered by a physician or caretaker in the patient information. The keywords may be matched with questions. In an embodiment, a vector analysis between the patient information and questions may be performed, and questions are selected based on a distance between a vector of patient information and a vector of a question.

At optional S530, one or more suggestions may be generated for possible questions to add to the questionnaire based on the selected questions, the received patient information input, or both. The generated suggestions may be provided, for example, to a user of a PCD.

FIG. 7 shows a non-limiting example of a questionnaire 700. Questionnaire 700 may include a plurality of sections 702 (e.g., main complaints, prior sleep disorder diagnosis or studies, sleep pattern, breathing, daytime sleepiness), check boxes 704, fill in the blank answer spaces 706, and/or instruction(s) 708. At least one section 702 may include one or more yes/no questions.

Figure 6:
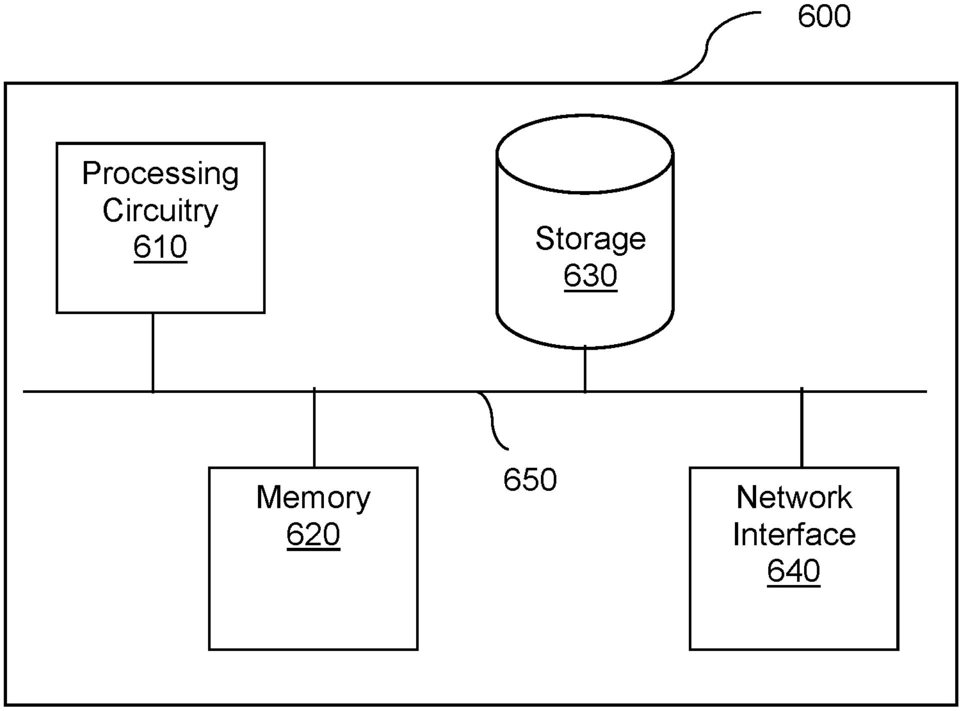
FIG. 6 is a schematic diagram of a hardware layer which may be configured for performing an at-home peripheral arterial tonometry test according to an embodiment.

FIG. 6 is an example schematic diagram of a hardware layer 600 which may be configured for performing an at-home peripheral arterial tonometry test according to an embodiment. The hardware layer 600 may be, for example but not limited to, the hardware layer of the user device 170 or the primary sensor device 160, FIG. 1.

The hardware layer 600 includes a processing circuitry 610 coupled to a memory 620, an optional storage 630, and a network interface 640. In an embodiment, the components of the hardware layer 600 may be communicatively connected via a bus 650.

The processing circuitry 610 may be realized as one or more hardware logic components and circuits. For example, and without limitation, illustrative types of hardware logic components that can be used include field programmable gate arrays (FPGAs), application-specific integrated circuits (ASICs), Application-specific standard products (ASSPs), system-on-a-chip systems (SOCs), graphics processing units (GPUs), tensor processing units (TPUs), general-purpose microprocessors, microcontrollers, digital signal processors (DSPs), and the like, or any other hardware logic components that can perform calculations or other manipulations of information.

The memory 620 may be volatile (e.g., random access memory, etc.), non-volatile (e.g., read only memory, flash memory, etc.), or a combination thereof.

In one configuration, software for implementing one or more embodiments disclosed herein may be stored in the storage 630. In another configuration, the memory 620 is configured to store such software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the processing circuitry 610, cause the processing circuitry 610 to perform the various processes described herein.

The storage 630 may be magnetic storage, optical storage, and the like, and may be realized, for example, as flash memory or other memory technology, or any other medium which can be used to store the desired information.

The network interface 640 allows the hardware layer 600 to communicate with, for example, the PCD 110, the question database 130, the medical databases 142 and 144, the admin device 150, or a combination thereof.

It should be understood that the embodiments described herein are not limited to the specific architecture illustrated in FIG. 6, and other architectures may be equally used without departing from the scope of the disclosed embodiments.

The various embodiments disclosed herein can be implemented as hardware, firmware, software, or any combination thereof. Moreover, the software is preferably implemented as an application program tangibly embodied on a program storage unit or computer readable medium consisting of parts, or of certain devices and/or a combination of devices. The application program may be uploaded to, and executed by, a machine comprising any suitable architecture. Preferably, the machine is implemented on a computer platform having hardware such as one or more central processing units ("CPUs"), a memory, and inpuUoutput interfaces. The computer platform may also include an operating system and microinstruction code. The various processes and functions described herein may be either part of the microinstruction code or part of the application program, or any combination thereof, which may be executed by a CPU, whether or not such a computer or processor is explicitly shown.

In addition, various other peripheral units may be connected to the computer platform such as an additional data storage unit and a printing unit. Furthermore, a non-transitory computer readable medium is any computer readable medium except for a transitory propagating signal.

All examples and conditional language recited herein are intended for pedagogical purposes to aid the reader in understanding the principles of the disclosed embodiment and the concepts contributed by the inventor to furthering the art, and are to be construed as being without limitation to such specifically recited examples and conditions. Moreover, all statements herein reciting principles, aspects, and embodiments of the disclosed embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

It should be understood that any reference to an element herein using a designation such as "first," "second," and so forth does not generally limit the quantity or order of those elements. Rather, these designations are generally used herein as a convenient method of distinguishing between two or more elements or instances of an element. Thus, a reference to first and second elements does not mean that only two elements may be employed there or that the first element must precede the second element in some manner. Also, unless stated otherwise, a set of elements comprises one or more elements.

As used herein, the phrase "at least one of" followed by a listing of items means that any of the listed items can be utilized individually, or any combination of two or more of the listed items can be utilized. For example, if a system is described as including "at least one of A, B, and C," the system can include A alone; B alone; C alone; 2A; 2B; 2C; 3A; A and B in combination; Band C in combination; A and C in combination; A, B, and C in combination; 2A and C in combination; A, 3B, and 2C in combination; and the like.

What is claimed is:

1. A method for performing a remote sleep apnea test, comprising:

generating, by a sensor assembly comprising a primary sensor device, a finger probe, and an accelerometer, sensor measurements during a remote sleep apnea test in a home of a patient;

determining, via a processing circuitry, an end of the remote sleep apnea test based on detecting cessation of sensor data from the sensor assembly;

receiving, based on at least one first input at a physician computing device remote from the home of the patient, at least one post-test question for the patient;

identifying a questionnaire for the patient, wherein the questionnaire is dynamically generated from a plurality of question groups based on the sensor measurements recorded during the remote sleep apnea test;

rendering the questionnaire, including the at least one post-test question, to the patient via a display communicatively connected to the sensor assembly upon determining the end of the remote sleep apnea test based on detecting the cessation of sensor data from the sensor assembly, causing the questionnaire to be made unavailable after a predetermined period of time has lapsed to prevent an inaccurate response to the at least one post-test question;

capturing, via an input interface communicatively connected to the sensor assembly, at least one second input provided by the patient in response to the rendered questionnaire before the questionnaire is made unavailable after the predetermined period of time;

generating a notification comprising the sensor measurements generated during the remote sleep apnea test and the at least one second input provided by the patient in response to the rendered questionnaire; and transmitting the notification comprising the sensor measurements and the at least one second input to the physician computing device remote from the home of the patient.

2. The method of claim 1, further comprising:

determining the at least one post-test question based on the sensor measurements generated during the remote sleep apnea test.

3. The method of claim 2, wherein the at least one post-test question is determined within a threshold period of time since the end of the remote sleep apnea test is determined.

4. The method of claim 3, wherein a respective timestamp is associated with each respective input of the at least one second input provided by the patient in response to the rendered at least one post-test question.

5. The method of claim 1, further comprising:

rendering at least one pre-test question via a user interface before the remote sleep apnea test; and capturing at least one input provided by the patient in response to the rendered at least one pre-test question.

6. The method of claim 5, wherein the at least one pre-test question comprises at least one first pre-test question and at least one second pre-test question, the method further comprising:

dynamically determining at least a portion of the at least one second pre-test question based on at least a portion of at least one input provided by the patient in response to the at least one first pre-test question.

7. The method of claim 5, wherein the at least one post-test question is determined based on at least one of: the at least one input provided by the patient in response to the rendered at least one pre-test question, the sensor measurements generated during the remote sleep apnea test, or any combination thereof.

8. The method of claim 5, wherein the at least one pre-test question comprises at least one first pre-test question and at least one second pre-test question, wherein capturing the at least one input provided by the patient in response to the rendered at least one pre-test question comprises capturing a response to the at least one first pre-test question and not the at least one second pre-test question, and wherein the at least one post-test question comprises the at least one second pre-test question.

9. The method of claim 1, wherein the sensor assembly comprises a first group of sensors and a second group of sensors, wherein the first group of sensors is activated at a beginning of the remote sleep apnea test, wherein the second group of sensors is configured in response to sensor signals captured by the first group of sensors.

10. The method of claim 1, wherein the at least one post-test question is rendered via the input interface when a challenge issued to the patient is successfully completed.

11. The method of claim 1, further comprising:

transmitting the sensor measurements and the at least one second input to a first database of a plurality of databases, wherein the first database is located in a jurisdiction of the patient.

12. The method of claim 1, wherein the sensor assembly comprises at least one of: a chest sensor, a photoplethysmogram (PPG) signal generator, a peripheral arterial tone (PAT) amplitude signal generator, or any combination thereof.

13. The method of claim 1, further comprising:

selecting the at least one post-test question based on the patient having one or more similar characteristics to patients of a patient cluster.

14. The method of claim 1, wherein the at least one post-test question comprises at least one first post-test question and at least one second post-test question, the method further comprising:

determining the first post-test question based on the sensor measurements generated during the remote sleep apnea test, wherein capturing the at least one second input provided by the patient in response to the rendered at least one post-test question comprises capturing at least one input provided by the patient in response to the first post-test question; and dynamically determining the second post-test question based on the sensor measurements generated during the remote sleep apnea test and at least a portion of the at least one second input provided by the patient in response to the first post-test question.

15. The method of claim 1, wherein the notification further comprises at least one of: comorbidity information based on the sensor measurements generated during the remote sleep apnea test, cross-reference information based on the sensor measurements generated during the remote sleep apnea test and at least one sleep study result model associated with a patient cluster, or any combination thereof.

16. The method of claim 1, further comprising determining a symptom that has a probability to occur based on cross-referencing the sensor measurements generated during the remote sleep apnea test and at least one sleep study result model associated with a patient cluster, wherein the notification comprises an indication of the symptom.

17. The method of claim 1, further comprising:

receiving, based on at least one third input at the physician computing device remote from the home of the patient, at least one second post-test question for the patient;

rendering the at least one second post-test question via the display communicatively connected to the sensor assembly.

18. The method of claim 1, wherein causing the questionnaire to be made unavailable after the predetermined period of time prevents input from the patient after the predetermined period of time has lapsed.

19. A system for performing a remote sleep apnea test, comprising:

a processing circuitry; and a memory, the memory containing instructions that, when executed by the processing circuitry, configure the system to:

generate, by a sensor assembly comprising a primary sensor device, a finger probe, and an accelerometer, sensor measurements during a remote sleep apnea test in a home of a patient;

determine, an end of the remote sleep apnea test based on detecting cessation of sensor data from the sensor assembly;

receive, based on at least one first input at a physician computing device remote from the home of the patient, at least one post-test question for the patient;

identify a questionnaire for the patient, wherein the questionnaire is dynamically generated from a plurality of question groups based on the sensor measurements recorded during the remote sleep apnea test;

render the questionnaire, including the at least one post-test question, to the patient via a display communicatively connected to the sensor assembly upon determining the end of the remote sleep apnea test based on detecting the cessation of sensor data from the sensor assembly, causing the questionnaire to be made unavailable after a predetermined period of time has lapsed to prevent an inaccurate response to the at least one post-test question;

capture, via an input interface communicatively connected to the sensor assembly, at least one second input provided by the patient in response to the rendered questionnaire before the questionnaire is made unavailable after the predetermined period of time;

generate a notification comprising the sensor measurements generated during the remote sleep apnea test and the at least one second input provided by the patient in response to the rendered questionnaire; and transmit the notification comprising the sensor measurements and the at least one second input to the physician computing device remote from the home of the patient.

20. The system of claim 19, wherein the memory contains instructions that, when executed by the processing circuitry, configure the system to:

determine the at least one post-test question based on the sensor measurements generated during the remote sleep apnea test.

21. The system of claim 19, wherein the memory contains instructions that, when executed by the processing circuitry, configure the system to:

render at least one pre-test question via a user interface before the remote sleep apnea test; and capture at least one input provided by the patient in response to the rendered at least one pre-test question.

22. The system of claim 21, wherein the at least one pre-test question comprises at least one first pre-test question and at least one second pre-test question, and wherein the memory contains instructions that, when executed by the processing circuitry, configure the system to:

dynamically determine at least a portion of the at least one second pre-test question based on at least a portion of at least one input provided by the patient in response to the at least one first pre-test question.

23. The system of claim 19, wherein the sensor assembly comprises a first group of sensors and a second group of sensors, wherein the first group of sensors is activated at a beginning of the remote sleep apnea test, wherein the second group of sensors is configured in response to sensor signals captured by the first group of sensors.

24. The system of claim 19, wherein the sensor assembly comprises at least one of: a chest sensor, a photoplethysmogram (PPG) signal generator, or a peripheral arterial tone (PAT) amplitude signal generator.

25. The system of claim 19, wherein the system is configured to:

select the at least one post-test question based on the patient having one or more similar characteristics to patients of a patient cluster.

26. A non-transitory computer readable medium having stored thereon instructions for causing a processing circuitry to execute a process, the process comprising:

generating, by a sensor assembly comprising a primary sensor device, a finger probe, and an accelerometer, sensor measurements during a remote sleep apnea test in a home of a patient;

determining, an end of the remote sleep apnea test based on detecting cessation of sensor data from the sensor assembly;

receiving, based on at least one first input at a physician computing device remote from the home of the patient, at least one post-test question for the patient;

identifying a questionnaire for the patient, wherein the questionnaire is dynamically generated from a plurality of question groups based on the sensor measurements recorded during the remote sleep apnea test;

rendering the questionnaire, including the at least one post-test question, to the patient via a display communicatively connected to the sensor assembly after upon determining the end of the remote sleep apnea test based on detecting the cessation of sensor data from the sensor assembly, causing the questionnaire to be made unavailable after a predetermined period of time has lapsed to prevent an inaccurate response to the at least one post-test question:

capturing, via an input interface communicatively connected to the sensor assembly, at least one second input provided by the patient in response to the rendered questionnaire before the questionnaire is made unavailable after the predetermined period of time;

generating a notification comprising the sensor measurements generated during the remote sleep apnea test and the at least one second input provided by the patient in response to the rendered questionnaire; and transmitting the notification comprising the sensor measurements and the at least one second input to the physician computing device remote from the home of the patient.

* * * * *